(12) United States Patent
Rimm et al.

(10) Patent No.: US 6,444,436 B1
(45) Date of Patent: *Sep. 3, 2002

(54) EVACUATED CONTAINER ASSEMBLY FOR ANALYSIS OF A BLOOD SAMPLE FOR THE PRESENCE OR ABSENCE OF RARE EVENTS

(76) Inventors: David L. Rimm, 15 Pawson Landing, Brandford, CT (US) 06405; Paul Fiedler, 90 Gilnock Dr., New Haven, CT (US) 06515; Robert A. Levine, 31 Pilgrim La., Guilford, CT (US) 06437; Stephen C. Wardlaw, Highrock, Lyme, CT (US) 06371

( * ) Notice: Subject to any disclaimer, the term of this patent is extended or adjusted under 35 U.S.C. 154(b) by 0 days.

This patent is subject to a terminal disclaimer.

(21) Appl. No.: 09/507,635

(22) Filed: Feb. 22, 2000

(51) Int. Cl.[7] .............................................. G01N 33/574
(52) U.S. Cl. ........................ 435/40.51; 356/36; 435/7.1; 435/7.22; 435/7.23; 435/7.24; 436/63; 436/64; 436/523; 436/810
(58) Field of Search ............................. 435/7.22, 7.23, 435/7.24, 7.1, 40.51; 436/63, 64, 523, 810; 356/36

(56) References Cited

U.S. PATENT DOCUMENTS

| | | | | |
|---|---|---|---|---|
| 5,342,790 A | * | 8/1994 | Levine et al. ................ | 436/523 |
| 5,403,714 A | * | 4/1995 | Levine et al. ................ | 435/7.2 |
| 5,460,979 A | * | 10/1995 | Levine et al. ................ | 436/523 |
| 5,496,704 A | * | 3/1996 | Fiedler et al. ............. | 435/7.22 |
| 5,723,285 A | * | 3/1998 | Levine et al. .................. | 435/4 |
| 5,759,794 A | * | 6/1998 | Levine et al. ............. | 435/7.24 |
| 5,776,710 A | * | 7/1998 | Levine et al. ............. | 435/7.24 |
| 5,830,639 A | * | 11/1998 | Levine et al. .................. | 435/4 |
| 5,834,217 A | * | 11/1998 | Levine et al. ............. | 435/7.24 |
| 6,197,523 B1 | * | 3/2001 | Rimm et al. ................ | 435/7.1 |

* cited by examiner

Primary Examiner—Christopher L. Chin
(74) Attorney, Agent, or Firm—William W. Jones

(57) ABSTRACT

A method for analyzing blood enables one to isolate, detect, enumerate and confirm under magnification the presence or absence of target cancer cells and/or hematologic progenitor cells, or other rare events which are known to circulate in blood. The analysis is performed in a sample of centrifuged anticoagulated whole blood. The analysis involves both morphometric and epitopic examination of the blood sample while the blood sample is disposed in a centrifuged blood sampling container. The epitopic analysis of the presence or absence of cancer cells relies on the detection of epitopes which are known to be present on cancer cells and not on normal circulating blood cells; and the epitopic analysis of the presence or absence of hematologic progenitor cells relies on the detection of epitopes which are known to be present on hematologic progenitor cells and not on normal circulating blood cells. The targeted epitopes on the target cell types are epitopes which are also known to be absent on normal circulating blood cells; and the target cancer cell epitopes are epitopes which are known to be absent on target hematologic progenitor cells. Fluorophors with distinct emissions are coupled with antibodies which are directed against the targeted epitopes. The morphometric analysis is performed by staining the cells in the blood sample with an intracellular stain, such as acridine orange, which highlights the intracellular cell structure. Both the morphometric and epitopic analyses are preferably performed in the expanded buffy coat layer in the centrifuged blood sample. The morphometric analysis and/or the epitopic analysis may be performed under magnification both visually and/or photometrically.

11 Claims, 4 Drawing Sheets

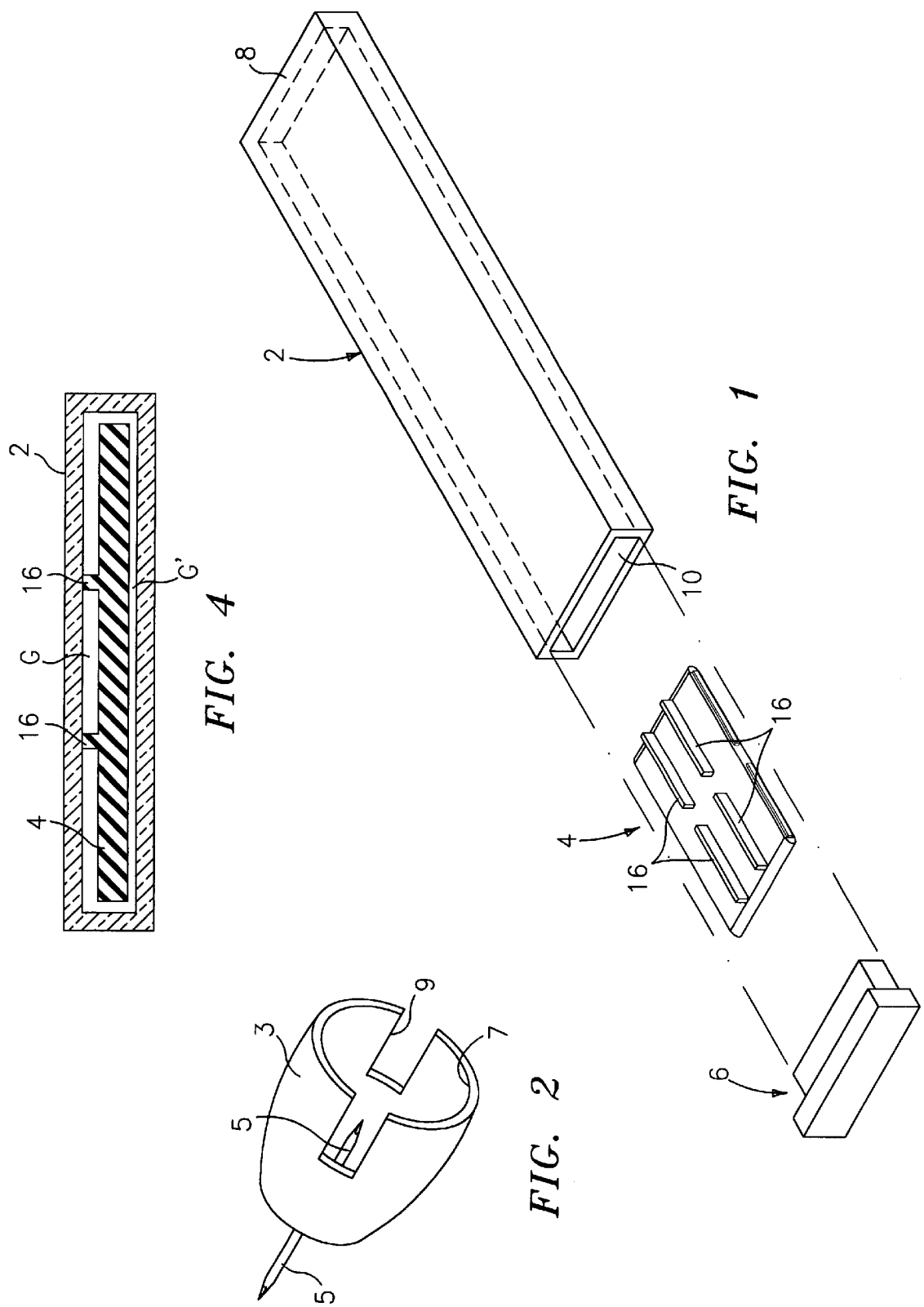

EVACUATED CONTAINER ASSEMBLY FOR ANALYSIS OF A BLOOD SAMPLE FOR THE PRESENCE OR ABSENCE OF RARE EVENTS

TECHNICAL FIELD

This invention relates to an evacuated container and method for use in analyzing a centrifuged anticoagulated whole blood sample for the presence or absence of rare events. More particularly, this invention relates to the detection of hematological rare events such as circulating cancer cells, bacteria, hemato-parasites, or other rarely occurring visually or photometrically detectable particles in the blood sample. A preferred embodiment of the container of this invention is an evacuated rectilinear container which contains an insert which container is essentially the same length and width as a microscope slide.

BACKGROUND ART

It is known that rare events, such as cancer cells may be present in the blood stream. Co-pending U.S. patent application Ser. No. 08/976,886, filed Nov. 24, 1997 describes a method for examining a centrifuged sample of anticoagulated whole blood for the presence or absence of cancer cells or other rare events. The method described in the aforesaid patent application involves the use of a capillary tube containing a cylindrical insert or float which restricts the available space in the tube into which the white cells and platelets will settle during centrifugation. This physically elongates the buffy coat portion of the blood sample and forces any cancer cells in the blood sample toward the tube wall where they can be seen under suitable magnification. We have discovered that any cancer cells present in the blood sample will settle into the area occupied by the buffy coat, and particularly in a region above the granulocytes and below the plasma, during centrifugation. The exact location of the cancer cells in the buffy coat will be governed by the density of the cancer cells and other less well-characterized physical forces.

The capillary tubes utilized in connection with the procedure described in the aforesaid patent application are capable of holding about 111 micro liters of blood. The frequency of cancer cells in peripheral blood can be as low as about one cancer cell per milliliter, and will be relatively dependent on the stage of the cancer in the patient being tested. Stated another way, a patient in an early stage of cancer is likely to have a much lower number of circulating cancer cells in an individual's peripheral blood than a patient in advanced stages of the disease, and a sample of less than about 111 μl of blood stands about a 90% chance of missing a rare event in the blood sample when the rare event occurs at a frequency of about 1 per ml of sample. The ability to examine larger samples of peripheral blood could enable earlier detection of the disease or other rare events. A larger tube and insert could be used to enable the examination of larger blood samples, but tubes produce spherical aberrations due to the curvature of the glass tube wall. It is also noted that the use of tubular containers requires that the container be examined throughout a 360° arc for the presence or absence of the rare events. This requires rotating the tube in the microscopical examining instrument.

It would be highly desirable to be able to examine larger blood samples in the same manner as provided by the capillary tubes and inserts, without encountering visual aberrations and without the need to rotate the sample chamber, and in which a standard microscope stage could be used without significant modification. However, tubular specimen sample containers can also be used in the performance of the method aspects of this invention.

DISCLOSURE OF THE INVENTION

This invention relates to an assembly for analyzing larger samples of anticoagulated whole blood for the presence or absence of circulating cancer cells or other rare events. The assembly comprises a hollow sample container which has essentially the same shape, length and width of a microscope slide, but which is thicker than a microscope slide. The hollow interior of the container can hold from about five to about ten milliliters of blood. One end of the container is sealed and the other end is closed by an elastomeric stopper. Obviously, both ends of the container could be closed by elastomeric stoppers if so desired. A relatively flattened rectilinear insert is disposed in the container and occupies between about 80–95%, and preferably about 90% of the volume of the portion of the interior of the container in the area occupied by the insert. The specific gravity or density of the insert is such that the insert will settle into or float in the packed red cell layer and be surrounded by the buffy coat constituents during centrifugation of the blood sample in the container. The interior of the container is evacuated so that blood will flow into the container as the result of a cannula puncturing the elastomeric closure. The container can be used to draw blood directly from a patient, or can be used to obtain the blood from a larger container such as a VACUTAINER® brand container sold by Becton Dickinson and Company. When the container assembly of this invention is used to draw blood directly from a patient, the testing reagents needed to anticoagulate the blood sample and detect the rare events in the blood sample can be pre-incorporated into the sample container assembly.

Reagents needed to identify rare events can include stains such as acridine orange which can highlight cell morphology; antibodies which are specific to surface receptors on cancer cells or other rare events; and stains which, when irradiated by light of appropriate wavelengths, will emit signals at wavelengths which can be photometrically and/or visually differentially detected over the background noise of emissions from the blood sample constituents such as white cells, cytoplasm, hemoglobin, and the like, which result when the blood sample is irradiated by such light sources.

The insert can include a structure which will skew the location of the insert inside of the container so that the majority of the white cell and platelet constituents will be located on one side of the rectilinear insert thereby enabling that portion of the buffy coat to be examined for the presence or absence of cancer cells, or other rare events without the need of rotating the container about its axis. Suitable skewing structures can include rails, hemispherical bumps, fins, or the like, on the insert or on the interior of the container. The container assembly is preferably sized so as to be positionable in a conventional centrifuge, and also positionable on a conventional microscope stage.

It is therefore an object of this invention to provide an evacuated anticoagulated whole blood sampling container assembly, which can be centrifuged, which container assembly is rectilinear in configuration, and which container assembly includes a volume-occupying insert that restricts the volume available in the container assembly wherein rare events will settle during centrifugation of the blood sample in the container assembly.

It is a further object of this invention to provide a method for examining a centrifuged anticoagulated whole blood sample under suitable sample illumination conditions that will reveal the presence or absence of rare events, such as cancer cells in predetermined areas of the blood sample.

BRIEF DESCRIPTION OF THE DRAWINGS

These and other objects and advantages of the invention will become more readily apparent from the following detailed description of several embodiments of the invention when taken in conjunction with the accompanying drawings in which:

FIG. 1 is an exploded perspective view of one embodiment of a blood sampling container assembly formed in accordance with this invention;

FIG. 2 is a perspective view of a cannula assembly which may be used in conjunction with the assembly of FIG. 1 to draw blood into the assembly;

FIG. 4 is a transverse cross sectional view of of the container assembly of FIG. 1 illustrating how the insert is oriented in the container before and after centrifugation of the blood sample in the container assembly;

DETAILED DESCRIPTION OF SPECIFIC EMBODIMENTS OF THE INVENTION

Figure 3:
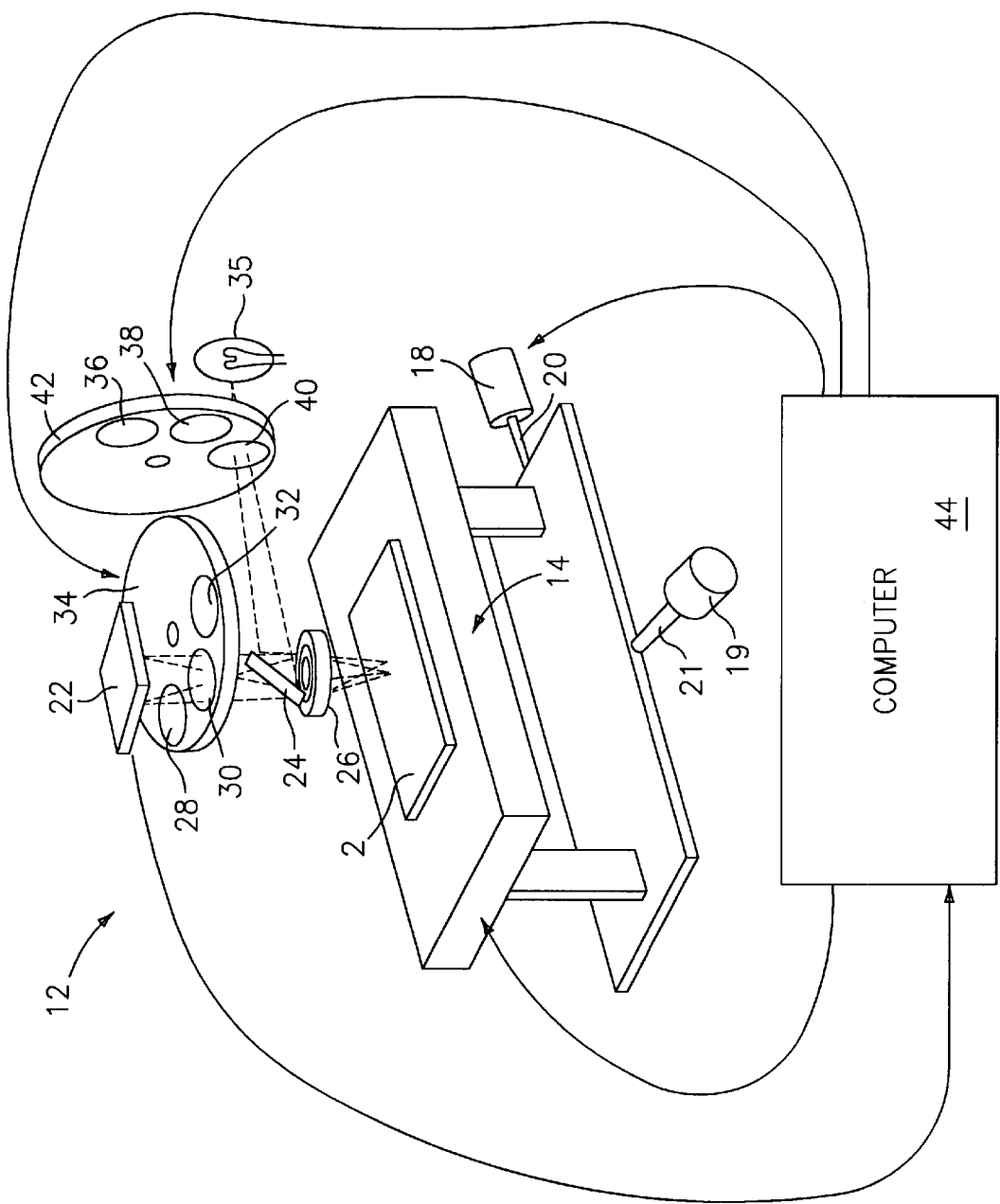
FIG. 3 is a schematic view of an instrument assembly which may be used to scan the blood sample in the sampling container assembly for the presence or absence of rare events.

Referring now to the drawings, there is shown in FIG. 1 a preferred embodiment of a blood sampling and analyzing container assembly which is formed in accordance with this invention. The assembly includes a hollow rectilinear container 2 and a rectilinear insert 4 which fits inside of the container 2. The container 2 has a sealed end 8 and an open end 10. The open end 10 of the container 2 is closed off by an elastomeric plug 6 which seals the open end 10 of the container 2. The insert 4 may include skewing structures such as rails 16 which will serve to asymmetrically position the insert 4 in the inside of the container 2 when the insert 4 is placed in the container 2. The insert 4 also preferably is provided with beveled ends 5 which minimize the chance of cells or other formed bodies in the blood sample from stacking up on the ends of the insert 4 during the centrifugation step. The elastomeric plug 6 is pressed into the open end 10 of the container 2 after the insert 4 has been inserted therein. The container 2 can then be evacuated by an external evacuator which pierces the plug 6 to draw the vacuum. Alternatively, the container 2 may be plugged while it is in an evacuated enclosure. The blood sample may then be drawn into the container 2 by piercing the plug 6 with a cannula 5 which forms a portion of a blood drawing assembly cap 3 that fits over the plugged end of the container 2. The blood drawing assembly cap 3 includes the open ended cannula 5, and a circular open end 7 which can also accommodate a tubular blood tube. The open end 7 includes opposed slots 9 into which the rectilinear container 2 can be inserted so as to enable the inner end of the cannula to pierce the plug 6 during the blood drawing operation.

FIG. 3 is a schematic depiction of an automated colorimetric microscopical instrument assembly, which is denoted generally by the numeral 12, and which can be used to scan a centrifuged blood sample that is contained in the paraphernalia shown in FIG. 1, and can, without human intervention, colorometrically differentiate between different types of cells in the layers being scanned, and can create and store or transmit an image of the cells being scanned. The instrument assembly 12 includes a stage 14 on which the container 2 is positioned during the analysis procedure. Reversible electric motors 18 and 19 selectively rotate drive screws 20 and 21 in opposite directions so that the container 2 can be axially and transversely moved in one direction and then in the reverse direction. In this manner, the entire targeted area of the container 2 can be scanned by the instrument assembly 12. The automatic embodiment of the instrument assembly 12 includes a CCD camera 22 which, by means of a beam splitter 24 and lens 26, is focused upon the rectilinear sample-containing gap in the container assembly 2, which gap is located between the container interior wall and the outer surface of the insert 4. The camera 22 should preferably be able to image both at visible wavelengths when the system is used with a sample that utilizes an acridine orange morphological-clarifying dye, and at near infra-red wavelengths when used to detect the epitopic label. It will be appreciated that the operating range of the lens 26 will be at least equal to the thickness of the gap between the container bore and the insert 4 in the container 2. The CCD camera 22 can view and records images of the sample through a plurality of different emission light wave filters 28, 30 and 32 which may be mounted on a selectively rotatable filter wheel 34. The instrument assembly 12 also includes an excitation light source 35 which directs an excitation light beam at the sample container 2 through the beam splitter 24 and the focusing lens 26. A series of excitation light wave length filters 36, 38 and 40 are mounted on a selectively rotatable filter wheel 42. The excitation light beam is deflected by the beam splitter 24 toward the focusing lens 26, and is focused on the sample container 2 by the lens 26. Thus, the two filter wheels 34 and 42 allow one to selectively control and vary the wave length of the excitation light source, as well as the emitted light source. A preprogrammed microprocessor controller 44 is operable to selectively control the rotation of the sample container 2, the rotation of the filter wheels 34 and 42, and operation of the CCD camera 22. The controller 44 thus enables fully automatic operation of the instrument assembly 12 without the need of human intervention.

The method of this invention operates in the following manner to capture and record images of the results of scanning the blood sample contained in the container 2, or in a tubular container which contains an insert, for suspicious nucleated cells, and also for confirming the malignant or benign nature of observed suspicious cells in situ in the blood sample. A venous or capillary sample of anticoagulated whole blood is drawn into a sampling container and insert assembly. The blood sample will be admixed in the container, or prior to being drawn into the container, with a fluorescent morphological stain such as acridine orange, so that morphological characteristics of nucleated cells which are observed in the blood sample can be analyzed. When the blood sample is being assayed for the presence or absence of cancer cells, the blood sample is also admixed with an epithelial cell surface binding site-specific labeled ligand which is used to determine whether any suspicious cells noted in the blood sample are of epithelial origin. This confirmation procedure was chosen because all of the tumorous cancer cells which are being assayed are epithelial cells. Preferred antigens that are highly specific to surface binding sites on epithelial cells are EP-cam and E-cadherin. In order to tag any epithelial cells we prefer to use a label such as Cy5 or Cy7 which emits a signal when illuminated with an appropriate wavelength light source, which emitted signal has a wavelength that is preferably greater than about 650 nm. These are cyamine-base fluorescent dyes marketed by Amersham. The label is preferably conjugated directly to the E-cadherin or the EP-cam. The Cy5 or Cy7 is a marker that fluoresces at wavelengths which are higher than acridine orange-induced emissions from white cells and platelets in the buffy coat, and therefore the emission detection instrument will not be subjected to background noise from the acridine orange-induced emissions emanating from the conventional formed components of the buffy coat. The admixture of anticoagulated whole blood, acridine orange, and EP-CAM-Cy5, or E-cadherin-Cy5, conjugate is centrifuged for a time period of about five to about sixty minutes in the sample container/insert assembly. The centrifuged sample is then placed in the imaging instrument, and the instrument is turned on. The CCD camera will record images of the portion of the centrifuged blood sample as the latter is appropriately positioned relative to the focal plane of the camera. An image of the entire area of a target zone in the blood sample will thus be produced by the camera 22. Separate scans will be made, one of which will record the blood sample image as defined by an appropriate combination of one or more of the instrument's filters 28, 30, 32, 36, 38 and 40 which is selected so as to differentially fluoresce the acridine orange stain added to the sample. This scan will produce images of all nucleated cells in the zone of the blood sample being scanned. Another scan will record the blood sample image as defined by a second appropriate combination of one or more of the instrument's filters 28, 30, 32, 36, 38 and 40 which is selected so as to differentially fluoresce the EP-CAM-Cy5 (or E-cadherin-Cy5) conjugate, or other label such as Cy7. This scan will produce images of all of the nucleated cells in the scanned zone of the blood sample which are epithelial cells.

Additional filter combinations could be used for additional scans depending on what additional cellular information is being sought. Such additional useful information could include additional cancer cell-specific epitopes, such as: future organ-specific markers; current markers including prostate-specific membrane antigen; mammaglobin (breast cancer); carcino-embrionic antigen ("CEA" for colon and rectal cancers; CA125 (ovarian cancer); and other markers which will enable the cytopathologist to identify the origin of the cancer cells, i.e., whether they are prostate cancer cells, breast cancer cells, lung cancer cells, ovarian cancer cells, or the like, which epitopic information is presently available, or becomes known in the future. The aforesaid analysis of the blood sample can be made automatically by the instrument shown in FIG. 3, or it can be performed by visually scanning the sample. Scanning of the acridine orange-highlighted cells allows one to identify all of the nucleated cells in the scanned zone, and also allows one to analyze the morphology of the nucleated cells in order to identify any cells which appear to have a morphology which suggests malignancy. Scanning of EP-CAM-Cy5 highlighted cells allows one to identify which of the nucleated cells in the scanned zone are epithelial cells. Confirmation of the presence of an epithelial cell (EP-CAM-Cy5-highlighted) having abnormal cell morphology (acridine orange-highlighted) in the centrifuged blood sample alerts the cytopathologist to the strong likelihood of a cancerous tumor in the blood sample donor. A similar protocol can be employed to determine whether suspicious nucleated cell are hematologic progenitor cells.

Referring now to FIG. 4, there is shown a cross sectional view of the container 2 and the insert 4 positioned inside of the container 2. It will be noted that the insert 4 and the container's inner wall combine to form a gap G, G' into which the white cells, platelets and cancer cells or other particulate rare events will localize during centrifugation of a blood sample in the container 2. When assaying the blood sample for the presence or absence of circulating epithelial cancer cells, the specific gravity of the insert 4 is preferably such that it will sink slightly into the red cell layer and extend upwardly into the plasma layer of the centrifuged blood sample. The insert 4 thus extends through the entirety of the centrifuged buffy coat and serves force the components of the buffy coat, i.e., white cells, platelets and cancer cells (if present) into the gap G, G'. If the rails 16 are formed on the insert 4, then the position of the insert 4 in the container 2 will be skewed to one side of the container 2 so that the thickness of the gap G will be larger than the thickness of the gap G'. In this embodiment of the apparatus of this invention, only the gap G is examined for evidence of rare events, since the volume of blood in the gap G' will be too small to allow entry of many rare events such as cancer cells, and since the majority of the buffy coat is present on the surface being examined. The thickness of the gap G will be in the range of about 30 $\mu$ to about 150 $\mu$, and is preferably about 50 $\mu$. An advantage of this construction is that the sample container 2 need not be turned over during the examination of its contents, but if so desired, both gaps G and G' could be examined. If the rails 16 are not included on the insert 4, then both gaps G and G' will definitely be examined.

Figure 5:
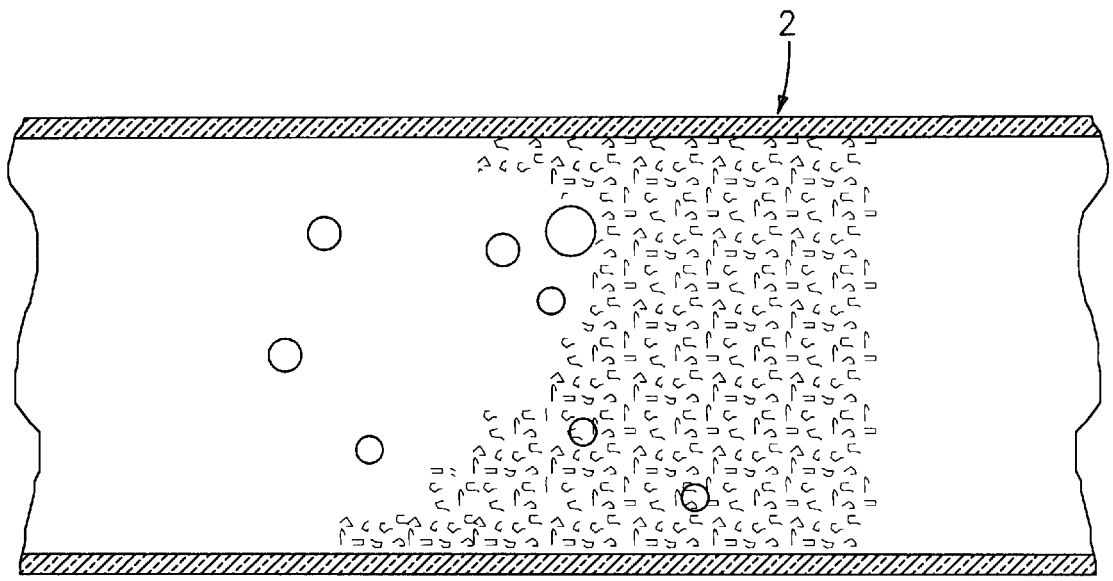
FIG. 5 is a fragmented sectional plan view of the area of the centrifuged blood sample wherein the cancer cells or other indicia of other rare events will localize during centrifugation of the blood sample in the container assembly, and be detectable and identifiable when the area is illuminated by a light source of a first wavelength which wavelength is non-specific to cancer cells or other rare events but is specific to a morphologically-highlighting label.
Figure 6:
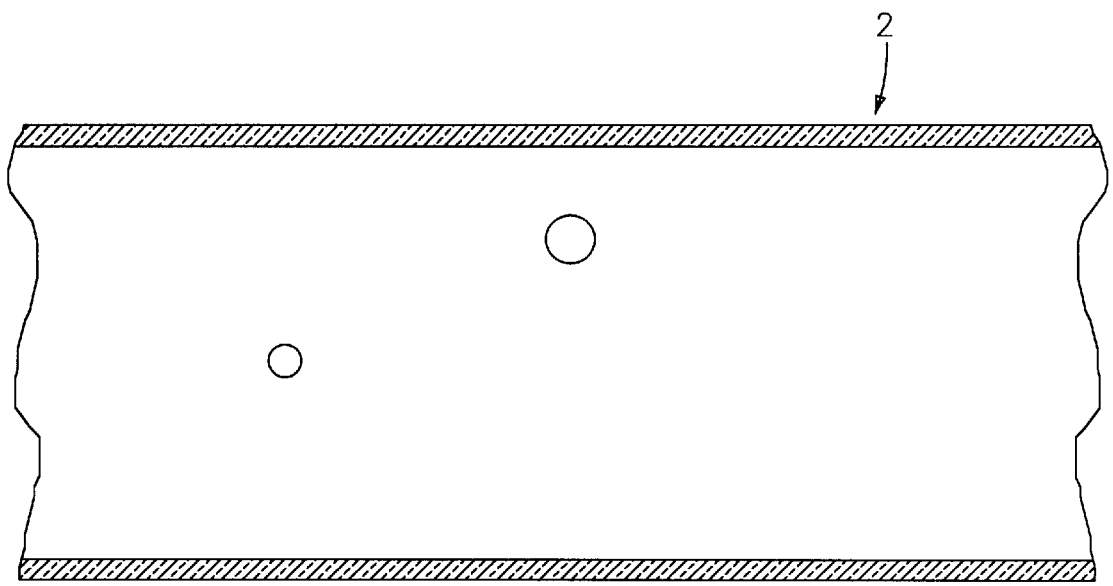
FIG. 6 is a view similar to FIG. 4 but showing the same area irradiated by a light source of a second wavelength which is specific to a different label that is attached to a ligand directed against a binding site on a cancer cell or other rare event.

FIGS. 5 and 6 are illustrative of recorded images of acridine orange-stained circulating prostate cancer cells in a blood sample taken from a patient known to be suffering from prostate cancer. The cancer cells were seen to be concentrated near the platelet-plasma interface, and in other locations in the buffy coat. FIG. 5 shows the cancer cells morphologically highlighted by acridine orange; and FIG. 6 shows the cancer cells epitopically highlighted by the EP-CAM-Cy5 conjugate. Thus, FIG. 5 confirms the presence of nucleated cells in the plasma layer adjacent to the platelet layer of the centrifuged blood sample; and FIG. 6 confirms that certain ones of the detected nucleated cells are epithelial cells. Visual analysis of the highlighted cells made in situ in the sample confirmed that they were malignant. The fact that not all cells are highlighted by Cy5 or Cy7 markers provides an internal negative control which confirms that the epitopically highlighted cells are epithelial in origin. Non-epitopically highlighted nucleated cells are lymphocytes.

Figure 7:
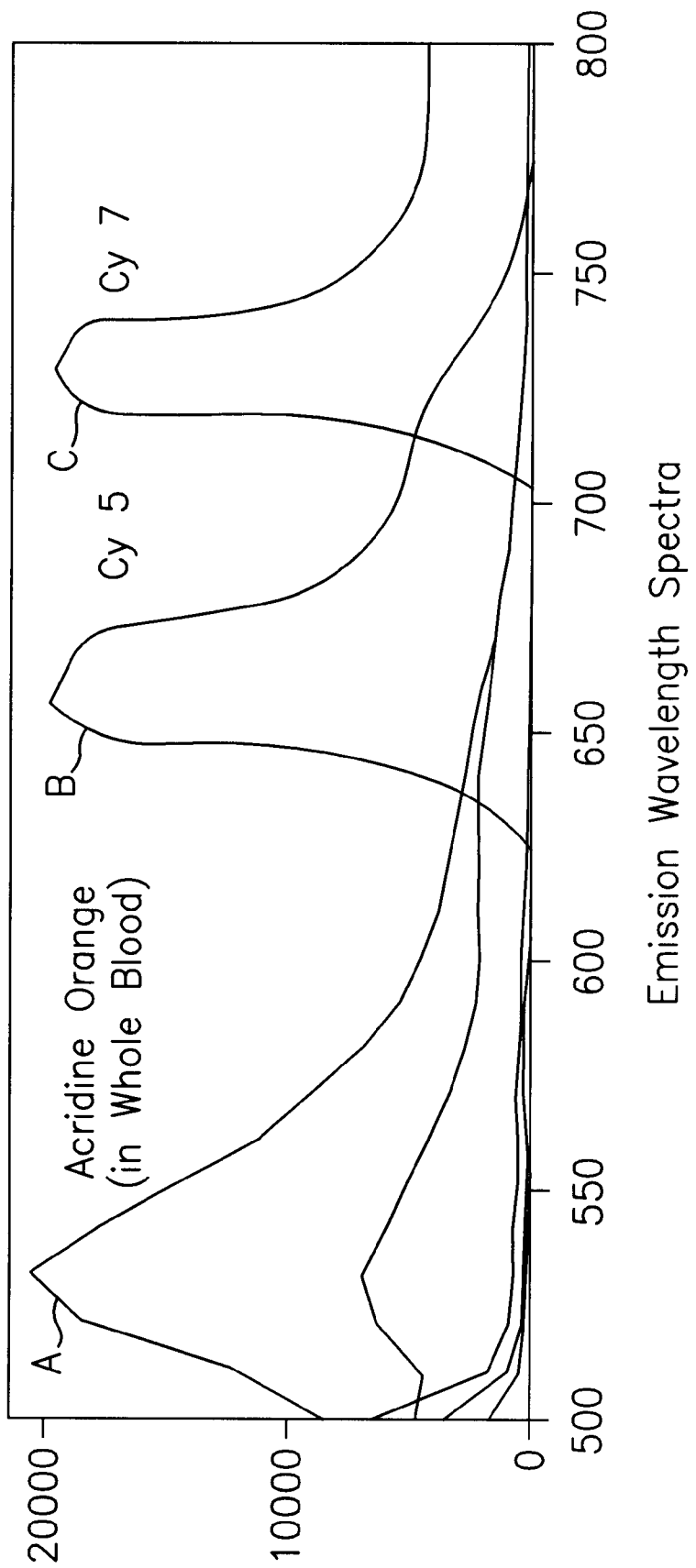
FIG. 7 is a trace of the emission wavelength peaks for the first light source, and for two labels which can be utilized with the second light source.

FIG. 7 is a schematic representation of the various dye emission wavelength peaks for the dyes which are preferred in performing the subject matter of this invention. The emission wavelength peaks of the dyes which are preferred for use in connection with this invention are greater than about 650 nm. The emission peak trace A represents the wavelength at which the emissions from acridine orange peak emanating from the nucleus of the cells, which peaks at about 540 nm; the emission peak trace B represents the wavelength at which the emissions from Cy-5 peak, which is approximately 650 nm; and the emission peak trace C represents the wavelength at which the emissions from Cy-7 peak, which is is approximately 730 nm. It is noted from FIG. 7 that the signals A, B and C will not interfere with each other since they contain minimal overlap.

It will be readily apparent that the assembly of this invention allows the examination of larger volumes of anticoagulated whole blood for the presence or absence of rare events, such as cancer cells. The assembly is amenable to centrifugation on a conventional centrifuge; and can be examined on a standard size microscope stage. The container assembly is pre-evacuated and can be used to draw blood directly from a patient, or from an interim blood drawing tube. The assembly can be modified so as to require examination of only one side of the blood sample if so desired. The planar geometry of the wall through which the blood sample is examined avoids spherical aberrations which are present when cylindrical tubes are used. The ability of the container to examine larger blood samples than are presently examined following the dictates of the prior art, enables the system to detect rare events which may occur in the blood at a frequency of less than 10/ml. Extremely rare events include bacteria and the protozoan hemoflagellate Trypanosoma cruzi, which is the cause of Chagas' disease, which may occur in the blood sample at frequencies of less than about 1/ml of the blood sample. The procedure of this invention allows a 10 ml blood sample to be examined for the presence or absence of such extremely rare events thereby allowing diagnosis of very difficult to diagnose diseases. These extremely rare events can be differentially highlighted by means of fluorescently labeled antibodies which are specific to the target rare events. Alternatively, non-specific stains such as acridine orange, or the like, could also be used to enhance the sensitivity of the detection method of such extremely rare events. The size of the blood sample which the container can hold can be between about 1 ml to about 15 ml, and may be directly related to the relative rarity of the target analytes for which the blood sample is being analyzed.

Since many changes and variations of the disclosed embodiments of the invention may be made without departing from the inventive concept, it is not intended to limit the invention except as required by the appended claims.

What is claimed is:

1. A method for detecting the presence or absence of circulating target nucleated cancer and/or hematologic progenitor cells in an anticoagulated whole blood sample, said method comprising the steps of:
    a) providing a transparent flattened rectilinear container which is approximately the same size in plan view as a microscope slide, said container having an interior cavity containing a flattened rectilinear insert, said container and insert combining to form a well-defined zone in the container, said container having opposed planar surfaces through which the blood sample can be examined;
    b) combining the blood sample with a target nucleated cell epitope-specific labeling agent so as to differentially distinguish any target nucleated cells which are present in the blood sample from other nucleated cells present in the blood sample;
    c) combining the blood sample with a colorant which is operable to clarify cell morphology in all nucleated cells present in the blood sample;
    d) placing the blood sample in the container and centrifuging the blood sample in the container so as to cause any target nucleated cells present in the blood sample to situate in said well-defined zone in the container;
    e) enumerating any differentially distinguished target nucleated cells found in the well-defined zone in the container;
    f) examining cell morphology of any differentially distinguished target nucleated cells situated in the well-defined zone in the container;
    g) said combining steps being performed either before or after the blood sample is placed in the container; and
    h) said enumerating and examining steps being performed in no particular order.

2. The method of claim 1 wherein said colorant has a first emission signal wavelength peak, and said labeling agent has a second emission signal wavelength peak, and wherein said first and second signal wavelength peaks are sufficiently different from each other so as to minimize emission signal overlap whereby signals emitted from said colorant do not interfere with signals emitted from said labeling agent.

3. The method of claim 2 wherein said colorant is acridine orange.

4. The method of claim 2 wherein said labeling agent is Cy5 or Cy7.

5. The method of claim 1 wherein said insert is asymmetrically positioned in said container so as to be closer to one of said planar surfaces than to the other of said planar surfaces.

6. A method for detecting the presence or absence of circulating target nucleated cancer and/or hematologic progenitor cells in an anticoagulated whole blood sample, said method comprising the steps of:
    a) providing a transparent container having a cavity containing an insert, said container and insert combining to form at least one well-defined zone in the container cavity;
    b) combining the blood sample with one or more epitope-specific labeling agents so as to differentiate any target nucleated cells in the blood sample;
    c) combining the blood sample with a colorant which is operable to clarify cell morphology in all nucleated cells in the blood sample;
    d) said colorant having a first emission signal wavelength peak, and said labeling agents having having a second emission signal wavelength peak, said first and second emission signal wavelength peaks being sufficiently different from each other so as to minimize emission signal overlap whereby signals emitted from said colorant do not interfere with signals emitted from said labeling agents;
    e) placing the blood sample in the container and centrifuging the blood sample in the container so as to cause any target nucleated cells present in the blood sample to gravitate by density into said well-defined zone in the container;
    f) enumerating any differentiated target nucleated cells found in situ in said well-defined zone in the container;
    g) examining the cell morphology of any differentiated target nucleated cells in situ in the well-defined zone in the container;
    h) said combining steps being performed either before or after the blood sample is placed in the container; and
    i) said enumerating and examining steps being performed in no particular order.

7. The method of claim 6 wherein said colorant is acridine orange.

8. The method of claim 7 wherein said labeling agent is Cy5 or Cy7.

9. A method for detecting the presence or absence of circulating target nucleated cancer and/or hematologic progenitor cells in an anticoagulated whole blood sample, said method comprising the steps of:

a) providing a transparent flattened rectilinear container which is approximately the same size in plan view as a microscope slide, said container having an interior cavity containing a flattened rectilinear insert, said container and insert combining to form a well-defined zone in the container, said container having at least one planar surface through which the blood sample can be examined;

b) combining the blood sample with at least one target nucleated cell epitope-specific labeling agent so as to differentially distinguish any target nucleated cells which are present in the blood sample from other nucleated cells present in the blood sample;

c) placing the blood sample in the container and centrifuging the blood sample in the container so as to cause any target nucleated cells present in the blood sample to situate in said well-defined zone in the container; and d) identifying any differentially distinguished target nucleated cells found in the well-defined zone in the container.

10. The method of claim 9 wherein said cavity is sized to contain about ten milliliters of blood.

11. A method for detecting the presence or absence of circulating target nucleated cancer and/or hematologic progenitor cells in an anticoagulated whole blood sample which target nucleated cells may occur in the blood sample at frequencies as low as about one occurrence per milliliter of blood, said method comprising the steps of:

a) providing a transparent flattened rectilinear container which is approximately the same size in plan view as a microscope slide, said container having an interior cavity which is sized to contain between about one and about ten milliliters of blood and which contains a flattened rectilinear insert, said cavity and insert combining to form a well-defined zone in the cavity, said container having at least one planar surface through which the blood sample can be examined with minimal optical distortion;

b) combining the blood sample with at least one target nucleated cell epitope-specific labeling agent so as to differentially distinguish any target nucleated cells which are present in the blood sample from other nucleated cells present in the blood sample;

c) placing the blood sample in the container and centrifuging the blood sample in the container so as to cause any target nucleated cells present in the blood sample to situate in said well-defined zone in the container, said combining and said placing steps being performed in no particular order; and d) identifying any differentially distinguished target nucleated cells found in the well-defined zone in the container.

* * * * *